United States Patent [19]

Siegel

[11] Patent Number: 5,224,349

[45] Date of Patent: Jul. 6, 1993

[54] REGULATED DISPOSABLE BODY ENDOTHERMIC COOLER

[76] Inventor: Israel Siegel, 2980 Point East Dr., Apt. D-612, N. Miami Beach, Fla. 33160

[21] Appl. No.: 797,187

[22] Filed: Nov. 25, 1991

[51] Int. Cl.⁵ .............................................. F25D 5/02
[52] U.S. Cl. ........................................ 62/4; 62/259.3; 126/204; 126/263
[58] Field of Search ................... 62/4, 259.3; 126/204, 126/263

[56] References Cited

U.S. PATENT DOCUMENTS

| | | | |
|---|---|---|---|
| 2,429,973 | 11/1947 | Alexander | 126/204 |
| 2,855,758 | 10/1958 | Johnson | 62/259.3 |
| 3,212,286 | 10/1965 | Curtis | 62/259.3 |
| 4,186,746 | 2/1980 | Byler | 126/263 |
| 5,062,269 | 11/1991 | Siegel | 62/4 |

Primary Examiner—Albert W. Davis, Jr.

[57] ABSTRACT

The body cooler consists of a wearable network of coils which contain a solid which absorbs heat when dissolved in water. The cooling action is initiated by the addition of water to the network through more than one conduit communicating between the portions of the network and a water source. The degree cooling is regulated by opening of closing of individual conduits which conduct the water to the portions of the network.

3 Claims, 1 Drawing Sheet

REGULATED DISPOSABLE BODY ENDOTHERMIC COOLER

BACKGROUND AND OBJECTIVES

The invention relates to micro-climate cooling devices and in particular to improvements in a wearable cooling system described by the present author in a U.S. Pat. No. 5,062,269. Essentially, the patent described a disposable cooling system that can be worn like a vest, and travel with the person using the cooling system. It is based upon the principle that certain solid substances induce an endothermic reactions, which absorb heat from the environment, when dissolved in water. In the previous invention the solid endothermic component has been distributed evenly in a network of pockets and coils which fit body contour. The cooling action of the vest was initiated by the transfer of water into the network through a tube which communicated between a water source and the network. A shortcoming in the cooling system has been the fact that it lacked means for regulating the degree of cooling. The main objective of the present invention is to provide a disposable wearable cooling device in which the degree of cooling can be regulated according to the individual preference of the user. An additional objective is to provide means to prolong the cooling periods by individual wearable cooling devices.

SUMMARY

A network of intercommunicating flexible containers in the shape of tubes and pockets are adapted to fit body contour. The pockets contain a solid reactant which absorbs heat when mixed with water. To activate the cooling system the water is transferred to the pockets through several conduits which conduct the water to the pockets. Each individual conduit has access to only a limited number of pockets which are evenly distributed throughout the cooling area. By opening and closing of the individual water conduits before the transfer of water into the system it is possible to control the number of pockets which receive the water, and thus regulate the degree of cooling by the wearable cooling system.

FIG. 1 is a cross sectional view of an embodiment of a regulated endothermic body cooler.

DETAILED DESCRIPTION

Figure 1:
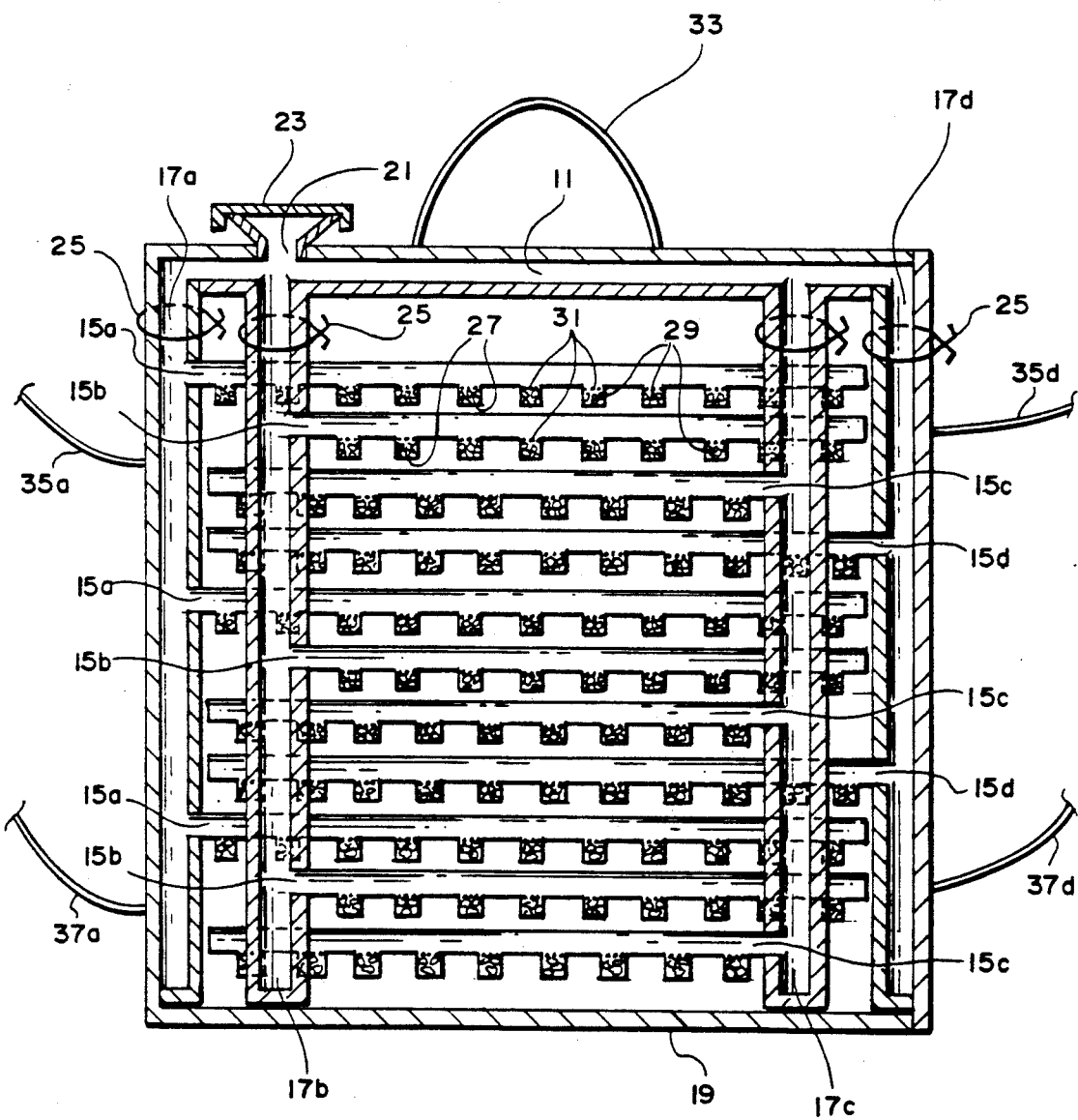

FIG. 1 illustrates the basic structures of an embodiment of a cooling vest. As shown in the figure, there is present a network of intercommunicating containers in the shape of horizontal and vertical conduits and pockets. The horizontal conduits include a top horizontal tube 11 and horizontal tubes 15a, 15b, 15c, and 15d. The vertical conduits consist of tubes 17a, 17b, 17c, and 17d. The arrangement is that the vertical tubes open into top horizontal tube 11. The bottoms of the vertical tubes are closed and are attached to a bottom flexible rubber, or plastic base 19. Horizontal tubes 15a–d are open at one end and closed at the other end. The open ends of horizontal tubes 15a are attached to vertical tube 17a and open into the vertical tube 17a. The closed ends of tubes 15a are attached to the outside wall of vertical tube 17d, and do not communicate with tube 17d. The open ends of horizontal tubes 15b are attached to vertical tube 17b and open into the vertical tube 17b. The closed ends of tube 15b are attached to the outside wall of vertical tube 17d, and do not communicate with tube 17d. The open ends of horizontal tubes 15c are attached to vertical tube 17c and open into the vertical tube 17c. The closed ends of tube 15c are attached and to the outside wall of vertical tube 17a, and do not communicate with tube 17a. The open ends of horizontal tubes 15d are attached to vertical tube 17d and open into the vertical tube 17a. The closed ends of tubes 15d are attached to the outside wall of vertical tube 17a, and do not communicate with tube 17a. Communicating with the top horizontal tube 11 is an inlet tube 21. As seen, the inlet tube 21 is shaped like a funnel to facilitate the intake of water into tube 11. A removable cover 23 open and closes inlet tube 21. Present on the top outside wall of each of vertical tubes 17a–d is a clamp 25. The clamps serve to close the communication of vertical tubes 17a–d with horizontal tube 11. Each clamp can be selectively removed manually to open any of tubes 17a–d.

Present between horizontal tubes 15a–d are vertical coils 27. The arrangement is that the vertical coils open at their upper end into the bottom portion of horizontal tubes 15a–d. The lower end of the vertical coils is closed. This enables the vertical coils to function as small receptacles or pockets. The length of the vertical pockets is such that they fit between the spaces of horizontal tubes 15a–d. Present inside pockets 27 are granules of amonium nitrate 29. The amonium nitrate granules function to induce an endothermic reaction upon the addition of water, as will be explained. Present on top of pockets 27 are screens 31. The arrangement is that the holes of the screens are smaller than the diameter of granules 29. The screens prevent the exit of of the granules from the vertical tubes, but allow the passage of liquids into the tubes. Thus, the vertical pockets serve to distribute granules 29 in fixed even positions in the network which function as evenly distributed cooling foci as will be described.

A strap 33 is attached to the top horizontal tube 11. The arrangement is that the strap forms a loop that can be worn on the neck of the person using the body cooler. Attached to the the side top corner of tube 17a is a strap 35a. Attached to the side top corner of tube 17d is a strap 35d. Attached to the bottom side corner of base tube 17a is a strap 37a. Attached to the bottom side corner of tube 17d is a strap 37d. The upper straps 35a and 35d are adapted to loop around the back of the person in opposite directions, and to be tied to each other. The bottom straps 37a and 37d are likewise adapted to loop around the back of the person in opposite directions, and to be tied to each other. The length of the straps is such that as they loop around the back of the person using the vest they pull the vest in opposing directions. They, thus, stretch the flexible horizontal tubings 15a–d and bring about an even spread of the vertical pockets 27 around the body surfaces of the person wearing the vest.

Present outside of the vest is a standard portable water canteen (not shown). The canteen contains water, and is carried by the person (not shown) using the vest.

The horizontal and vertical tubes have a very large surface volume ratio, are flexible, and shaped to resemble a vest which fits body contour. For example, the tubes may consist of flexible nylon coils. The number and dimensions of pockets 27 should be planned to accommodate the volume of the cooling mixtures required. This would depend on the degree and duration of cooling required, For example, a total of about 24 thousand calories would be removed from the environment by a cooling mixture containing 500 ml of water and 500 g of ammonium chloride (Handbook of Chemistry and Physics, 44th edition, 1962, page 2403). Assuming that 25% of the pockets containing the endothermic solid component are accessible to each of the 5 vertical tubes 17a-d then 125 ml of water is required to activate the endothermic chemicals which become accessible by the opening of one clamp. Each clamp would then control the removal of 6,000 calories from the immediate body area.

The operation of the device by the person wearing the device is as follows. For a direct body heat removal the vest is worn in close proximity to body surfaces. For example, the vest may be worn on top of the undershirt of the person using the cooling device. The vest is positioned horizontally on the front surface of of the person using the vest through strap 33 which fits around the neck of the person using the vest. The vest is then positioned vertically by straps 35a, 35d, 37a, and 37d. One to 4 of clamps 25 are then opened. The number of clamps opened would depend on the amount and duration of cooling required. For a example, when an low degree of cooling is desired only one clamp is opened. When a moderate or high degree of cooling is desired 2 or 3 clamps are opened. For maximal cooling all 4 clamps are opened. Cover 23 is then removed and water, obtained from a portable canteen, or other sources. is poured into tube 21. As the water enters tube 21 it spreads in horizontal conduit 11 and enters the open vertical conduits 17a-d by force of gravity. The water then enters the horizontal tubes 15a-d which communicate with the open vertical conduit 17a-d which received the water. The water will then enter by force of gravity into the pockets 27 which communicate with the horizontal tube containing the water. The endothermic reactant 29 present in pockets 27 then dissolves in the water and cools the water in the pockets. The cold water absorbs heat from the walls of the pockets. The cold pocket walls then absorb heat from the user's body. The duration of the cooling effect by the vest would depend on the environmental and body temperature, and by the number of clamps opened by the user. For example, when all the clamps are opened simultaneously in an average summer day the user will obtain a relatively high degree of cooling for about 60 minutes. The user can, however, chose to open one clamp at a time, at 30-60 minute intervals, to obtain a lower level of cooling which would last 3-4 hours.

While the present embodiment described a vest which fits around the front of the body it is understood that a similar vest may be adapted to fit around the back of the body. The front and back vests may be worn simultaneously to obtain a cooling system which completely surrounds most of the body's surfaces. Other details such as the shape and composition of the tubes and pockets, or the chemical composition of the endothermic components, may be altered, without departing from the essence of the invention as set forth in the claims. It is likewise understood that variations in the shape and number of the tubes and pockets may be made without departing from the essence of the invention. For example, the number of tubes communicating between the water source and the pockets may be less or more than the 4 that have been illustrated in the present embodiment of the invention.

What is claimed is:

1. A disposable wearable cooling device said device consist of a network of intercommunicating containers,
   said network adapted to fit body contour,
   a solid component which induces an endothermic reaction when mixed with a liquid,
   means to fix said solid component in pre-determined locations in said containers to obtain a pre-determined distribution of said solid component in said network,
   more than one conduit communicating between said locations and a source of said liquid,
   each of said conduits designed to communicate with only a portion of said locations,
   and means to open and close said conduits to regulate the number of said locations activated by said liquid, and the degree of cooling by said cooling device.

2. An endothermic cooling device consisting of at least one solid and one liquid component,
   said solid component absorbs heat when dissolved in said liquid,
   said solid component distributed in pre-determined locations in intercommunicating containers,
   more than one conduit communicating between said locations and a source of said liquid,
   each of said conduits designed to communicate with only a portion of said locations,
   and means to open and close said conduits to regulate the number of said locations activated by said liquid, and the degree of cooling by said cooling device.

3. An endothermic cooling device consisting of at least two components,
   said components designed to absorb heat when mixed with each other,
   one of said components distributed in predetermined locations in inter-communicating containers in a cooling area,
   more than one conduit communicating between said locations and a source of the second said component,
   a communication between each source conduit and a portion of said locations,
   said locations of each said portion distributed over the entire said cooling area to obtain an absorption of heat from the entire cooling area by each portion,
   and means to open and close each individual source conduit to obtain a partial cooling through the entire cooling area by said communication through each source conduit.

* * * * *